US011112357B2

(12) United States Patent
Schultz et al.

(10) Patent No.: US 11,112,357 B2
(45) Date of Patent: Sep. 7, 2021

(54) METHOD FOR OBSERVING AN OBJECT

(71) Applicants: COMMISSARIAT A L'ENERGIE ATOMIQUE ET AUX ENERGIES ALTERNATIVES, Paris (FR); INTELLIGENCE ARTIFICIELLE APPLICATIONS, Montpellier (FR)

(72) Inventors: Emmanuelle Schultz, Saint Egreve (FR); Damien Decq, Grenoble (FR); Michel Roch, Saint Bres (FR)

(73) Assignees: COMMISSARIAT A L'ENERGIE ATOMIQUE ET AUX ENERGIES ALTERNATIVES, Paris (FR); INTELLIGENCE ARTIFICIELLE APPLICATIONS, Montpellier (FR)

( * ) Notice: Subject to any disclaimer, the term of this patent is extended or adjusted under 35 U.S.C. 154(b) by 75 days.

(21) Appl. No.: 16/473,508

(22) PCT Filed: Dec. 21, 2017

(86) PCT No.: PCT/FR2017/053769
§ 371 (c)(1),
(2) Date: Jun. 25, 2019

(87) PCT Pub. No.: WO2018/122505
PCT Pub. Date: Jul. 5, 2018

(65) Prior Publication Data
US 2019/0323959 A1    Oct. 24, 2019

(30) Foreign Application Priority Data

Dec. 26, 2016 (FR) ...................................... 1663397

(51) Int. Cl.
*G01N 21/51* (2006.01)
*G01N 21/25* (2006.01)
(Continued)

(52) U.S. Cl.
CPC ........... *G01N 21/51* (2013.01); *G01N 21/255* (2013.01); *G01N 21/274* (2013.01); *G01N 21/474* (2013.01); *G01N 2021/4709* (2013.01)

(58) Field of Classification Search
CPC ..................................................... G01N 21/47
See application file for complete search history.

(56) References Cited

U.S. PATENT DOCUMENTS 4,555,635 A * 11/1985 Yoshida ............... G01N 21/952
250/559.07
4,867,530 A * 9/1989 Sedlmayr ................. G02B 6/04
385/116
(Continued)

FOREIGN PATENT DOCUMENTS

EP    3 054 281 A1    8/2016
EP    3054281    *    8/2016
(Continued)

OTHER PUBLICATIONS

International Search Report dated Apr. 5, 2018 in PCT/FR2017/053769 filed Dec. 21, 2017.
(Continued)

*Primary Examiner* — Kara E. Geisel
(74) *Attorney, Agent, or Firm* — Oblon, McClelland, Maier & Neustadt, L.L.P.

(57) ABSTRACT

A device and method for observing an object, in particular a biological object, includes a light source able to illuminate a sample, and a screen lying between the light source and the object. The screen includes an aperture, through which propagates the illuminating beam produced by the light source and propagating toward the screen. Under the effect of the illumination, the object emits back-scattered radiation that propagates to the screen, the area of which is preferably larger than 100 cm$^2$. The projection of the back-scattered radiation onto the screen forms an image representative of
(Continued)

the back-scattered radiation, called a scattergram. An image sensor allows an image representative of the scattergram formed on the screen to be acquired.

23 Claims, 9 Drawing Sheets

(51) Int. Cl.
*G01N 21/27* (2006.01)
*G01N 21/47* (2006.01)

(56) References Cited

U.S. PATENT DOCUMENTS

| | | | | |
|---|---|---|---|---|
| 5,241,369 | A * | 8/1993 | McNeil | G01B 11/303 356/445 |
| 5,327,229 | A * | 7/1994 | Konno | H04N 9/312 348/742 |
| 5,528,422 | A * | 6/1996 | Roberts | B60Q 1/2665 359/583 |
| 5,912,741 | A * | 6/1999 | Carter | G01N 21/4738 356/445 |
| 5,963,335 | A * | 10/1999 | Boutelle | G01N 21/59 356/39 |
| 7,554,665 | B2 * | 6/2009 | Wadman | G01N 21/274 356/236 |
| 7,872,754 | B2 * | 1/2011 | Wadman | G01N 21/49 356/445 |
| 2004/0190008 | A1 * | 9/2004 | Mieher | G01N 21/95607 356/625 |
| 2007/0146703 | A1 | 6/2007 | Adams et al. | |
| 2008/0192258 | A1 | 8/2008 | Wadman | |
| 2017/0219485 | A1 | 8/2017 | Bae et al. | |

FOREIGN PATENT DOCUMENTS

| | | |
|---|---|---|
| WO | WO 2007/020554 A1 | 2/2007 |
| WO | WO 2016/054408 A2 | 4/2016 |

OTHER PUBLICATIONS

Kim, H. et al., "Reflected scatterometry for noninvasive interrogation of bacterial colonies," Journal of Biomedical Optics, vol. 21, No. 10, Oct. 2016, pp. 107004-1-107004-9, XP060075145.

International Search Report dated Apr. 9, 2016 in PCT/FR2017/053768, citing documents AA and AX therein, 3 pages.

Bae, E. et al. "Label-free light-scattering sensors for high throughput screening of microbes in food" In: High Throughput Screening for Food Safety Assessment. Biosensor Technologies, Hyperspectral Imaging and Practical Applications, Woodhead Publishing Series in Food Science, Technology and Nutrition, No. 262, XP055404709, 2015, 16 pages.

* cited by examiner

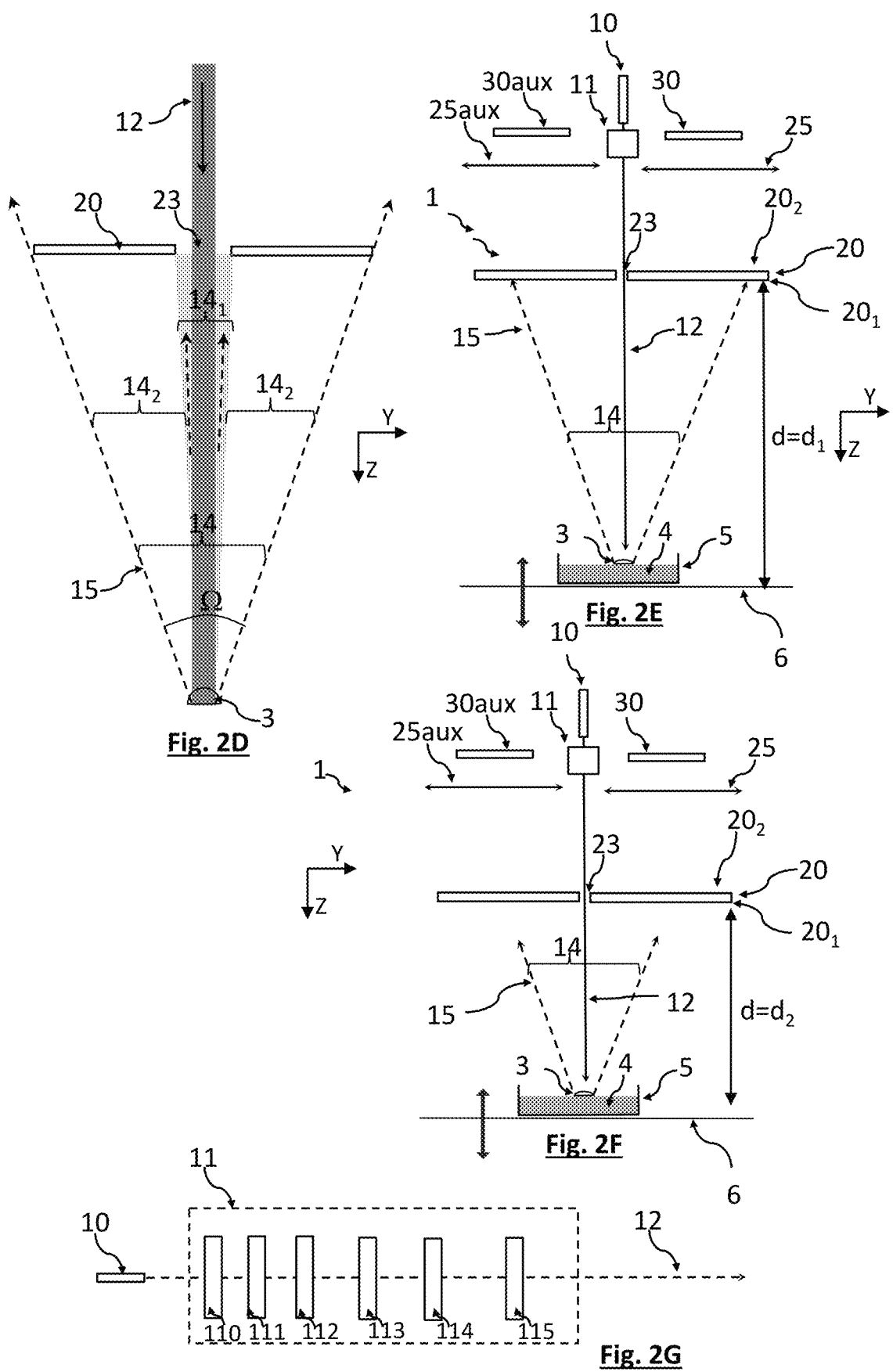

METHOD FOR OBSERVING AN OBJECT

TECHNICAL FIELD

The technical field of the invention is the observation and identification of an object, notably a biological object, in particular a bacterial colony, on the basis of an image of radiation back scattered by the object.

Prior Art

The identification of microorganisms, in particular bacteria, is a need that regards various fields. In the field of diagnostics, for example, the identification of bacteria allows the nature of the pathogens that are the root cause of an infection to be known, and the treatment of a patient to be optimized. Moreover, bacterial identification is a fundamental technique in epidemiology or in the fight against nosocomial infections. Beyond the health field, there are possible applications in, non-exhaustively, the hygiene, safety and food-processing fields.

Currently there are a variety of effective instruments allowing such an identification. The methods employed are in particular mass spectrometry, Raman spectroscopy, colorimetric tests, morphological analysis of colonies, or nucleic-acid amplification techniques. Methods employing a spectrometric or spectroscopic technique (mass spectrometry or Raman spectroscopy) require expensive apparatus and qualified operators. Colorimetric methods are simpler, but generally slower. As regards the amplification of nucleic acids, it requires many steps to be carried out in series while precise operating conditions are met.

The U.S. Pat. No. 74,665,560 describes a method allowing a microorganism to be characterized based on the exploitation of the scatter and diffraction, by the microorganism, of an incident laser beam. The microorganism is placed between a laser light source and an image sensor. Under the effect of an illumination by the laser beam, images are acquired in which diffraction patterns appear, the latter forming a signature of the observed microorganism. The U.S. Pat. No. 8,787,633 describes a method meeting the same objective. These documents describe a method for identifying bacteria that seems promising, but it becomes inapplicable if the medium in which the bacteria are placed is opaque, colored or scattering. Specifically, these methods use an image formed in a so-called transmission configuration, in which the sample is placed between a light source and an image sensor. If an exploitable image is to be obtained then the sample must be sufficiently 40 transparent. Thus, this method is not compatible with samples comprising a colored culture medium, for example the medium known as Columbia blood agar (CBA), which contains Columbia agar in sheep blood. It is also not applicable to a scattering medium such as cystine lactose electrolyte deficient (CLED) agar, or to an opaque medium such as chocolate agar. However, such culture media are very frequently (in about 70% of cases) used in clinical diagnostics.

Patent application WO2016/097063 partially addresses this problem, by proposing a method for observing microorganisms in which an image is formed not in a transmission configuration, but in a back-scatter configuration. The sample is illuminated by a laser beam. The back-scattered radiation is focused, by a collecting optic, onto an image sensor.

The document U.S. Pat. No. 5,241,369 describes a device allowing an image of radiation back scattered by a sample to be formed on a translucent screen, the latter being coupled to an image sensor. In this device, a light source illuminates a sample at an angle of incidence, the latter being inclined with respect to the optical axis of the image sensor.

The document WO2007/020554 describes a device for observing radiation scattered by a sample covered with a reflective screen. After multiple reflections, the image is focused on a convex reflector that is optically coupled to an image sensor. A similar configuration is described in U.S. Pat. No. 5,912,741.

The use of a translucent screen to observe light scattered by an object has also been described in the publication Huisung Kim et al "Reflected scatterometry for non invasive interrogation of bacterial colonies", International society for optical engineering, SPIE, vol. 21, no. 10, October 2016.

The inventors have implemented a method close to that described in WO2016/097063 and have observed certain limitations, which are described below. The objective of the invention is to overcome these limitations, by proposing a method for observing and characterizing microorganisms in a back-scatter configuration. The invention is particularly suitable for an opaque sample, while naturally remaining applicable to transparent samples. It allows colonies of microorganisms to be observed and characterized at various stages of development, independently of whether it is a question of microcolonies or macrocolonies. Another advantage is that it is simple to implement and robust, and does not require expensive instrumentation. Moreover, the method implemented is nondestructive. It may be applied to a colony, in its culture medium, without sampling being required. Lastly, the analysis is rapid, taking about one second.

SUMMARY OF THE INVENTION

The invention firstly relates to a device for observing an object, present in a sample, comprising:
  a holder, able to receive the sample;
  a light source, able to emit a light beam, called the incident light beam, in order to illuminate the object;
  an image sensor, for acquiring an image representative of radiation back scattered by the object under the effect of an illumination by the incident light beam;
the device being characterized in that it comprises:
  a screen, lying facing the holder, so as to be exposed to radiation back scattered by the object when the latter is illuminated by the incident light beam, so as to form, on the screen, an image, called a scattergram, representative of the back-scattered radiation;
  the screen comprising a first face, exposed to the back-scattered radiation;
  the screen lying between the light source and the object, the screen comprising an aperture, through which the incident light beam propagates before reaching the object;
  the image sensor being configured to acquire an image of the scattergram formed on the screen.

The light source may notably be a laser light source. The device may comprise a collimating optic, so that the light beam emitted by the light source is collimated. The device may comprise a beam-expanding optic, so as to adjust the diameter of the light beam to the size and morphology of the analyzed object.

The object may be a colony of microorganisms, for example a bacterial colony, in which case the screen allows a scattergram to be obtained the size of which is sufficiently large to characterize a colony at a sufficiently advanced stage of development.

The device may comprise any one of the following features, alone or in technically producible combinations:

The area of the first face of the screen is larger than 100 cm².

The diameter of the aperture is smaller than 2 cm.

The area of the aperture is smaller than 1 cm² or than 2 cm².

The screen has a curved shape, and notably curves toward the sample.

The screen comprises a second face, so that the scattergram formed on the first face appears on the second face; the screen then lies between the image sensor and the holder, such that the image sensor is coupled to the second face by a focusing optic.

The screen comprises a light guide for conveying light between the first face and the second face. The screen may notably comprise a plurality of optical fibers extending between the first face and the second face.

The screen transmits less than 90% of the back-scattered radiation from the first face to the second face.

The holder is movable with respect to the screen, the distance between the holder and the screen being able to be adjusted.

The device comprises an image sensor called the auxiliary image sensor, the auxiliary image sensor being configured to acquire an image, called the auxiliary image, of the scattergram formed on the screen, the screen being placed between the auxiliary image sensor and the object; the device also comprises a processor configured to combine the image acquired by the image sensor and the auxiliary image acquired by the auxiliary image sensor in order to form an image representative of the scattergram.

The image sensor is able to occupy various positions, and to acquire an image of the scattergram, formed on the screen, in each of the positions, the device also comprising a processor, able to process the image acquired by the image sensor in each position in order to form an image representative of the scattergram.

the incident beam propagates between the screen and the object about an axis called the axis of incidence, the device comprising what is called an annular reflector, lying around the axis of incidence, between the sample and the screen, the annular reflector being able to reflect some of the radiation back scattered toward the screen.

The device comprises a reflective element, able to direct the light beam emitted by the source, through the aperture, toward the object. In this case, the image sensor may be centered with respect to the axis of incidence along which the incident beam reaching the object propagates (or on the axis of back scatter about which the back-scattered radiation propagates).

Another subject of the invention is a method for observing an object present in a sample, the sample lying facing a screen comprising a first face, the method comprising the following steps:

a) illuminating the object using an incident light beam emitted by a light source, the screen lying between the light source and the object, the incident light beam propagating to the object through an aperture in the screen;

b) exposing a first face of the screen to light radiation back scattered by the sample, so as to form, on said first face, an image, called a scattergram, representative of said back-scattered radiation;

c) acquiring an image of the scattergram formed on the screen with an image sensor.

The method may comprise any one of the features described below, alone or in technically producible combinations:

the area of the aperture is smaller than 2 cm², or than 1 cm².

The area of the first face of the screen is larger than 100 cm².

The screen is curved, and notably curves toward the sample.

The screen comprises a second face, the screen lying between the image sensor and the sample, such that the image sensor is optically coupled to the second face by a focusing optic, the screen being such that the scattergram formed on the first face appears on the second face. The screen then acts as a back-lit screen as the scattergram, which is projected onto the first face, is transmitted to the second face.

The screen is translucent.

The screen comprises at least one light guide, notably an optical fiber, extending between the first face and the second face.

One face of the screen is structured so as to form a lens.

The screen transmits less than 90% of the back-scattered radiation.

The method comprises, following step c), a step of adjusting the distance between the sample and the screen depending on the image acquired by the image sensor, steps a) to c) being repeated after the adjustment of said distance.

Step c) comprises acquiring a plurality of images of the screen, each image being acquired from a different position with respect to the screen, and a step of combining the images thus acquired in order to establish an image, called the resulting image, of the scattergram formed on the screen.

The method comprises a step d) of characterizing the object on the basis of the image acquired by the image sensor, or on the basis of the resulting image. The characterization of the image may comprise:

determining characteristics of the image;

identifying the object using said characteristics and calibration characteristics established by implementing steps a) to c) of the method on a standard sample.

The object comprises a microorganism. The object may notably comprise a plurality of microorganisms forming a colony. The object may be a bacterial colony.

The method is implemented with a device such as described in the patent application.

Other advantages and features will become more clearly apparent from the following description of particular embodiments of the invention, which are given by way of nonlimiting example, and shown in the figures listed below.

FIGURES

Figures 2A, 2B, 2C:
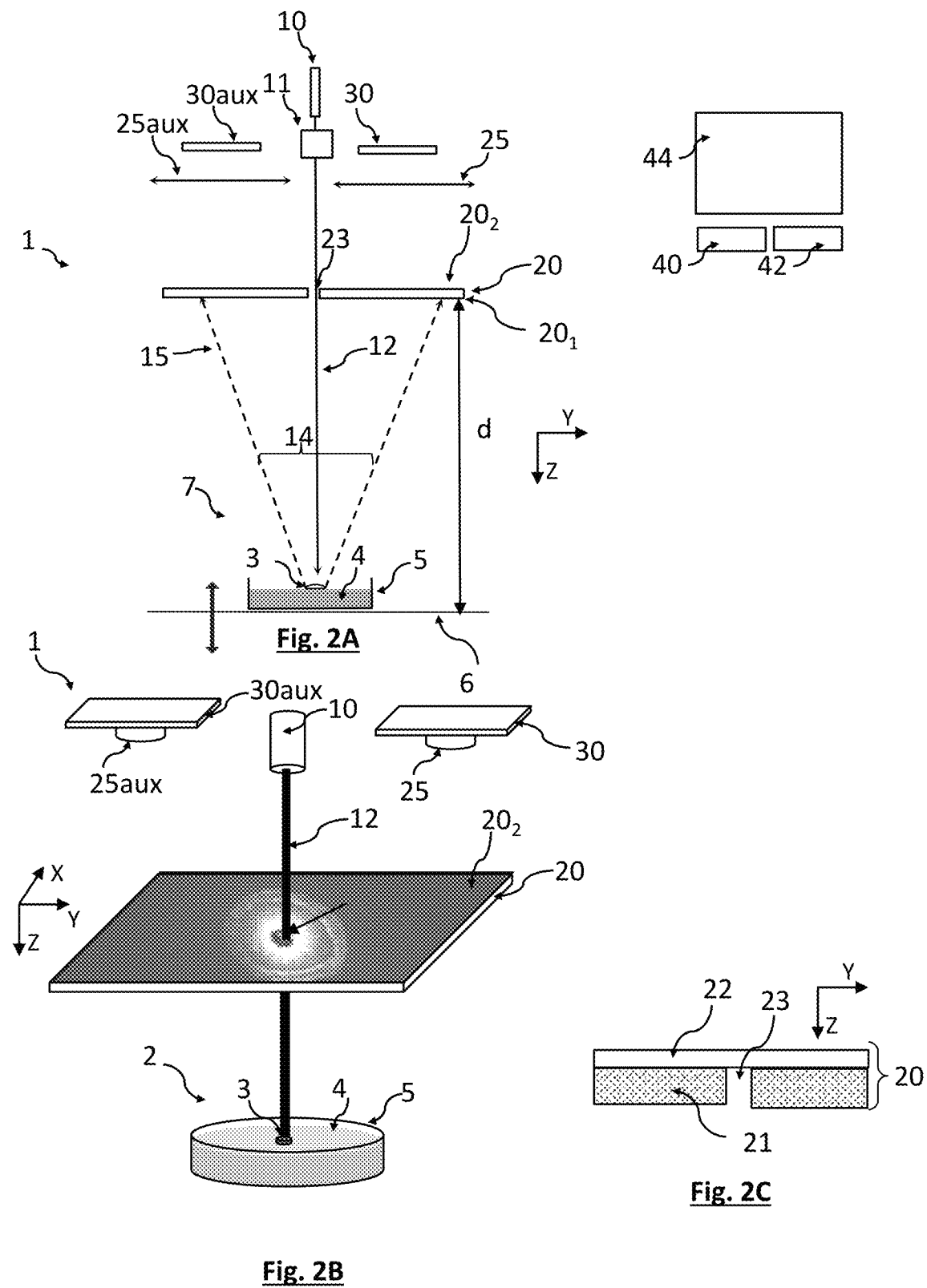

FIGS. 2A and 2B show one embodiment of the invention. FIG. 2C shows an example of a screen able to be implemented in the first, second or third embodiment. FIG. 2D is a detail of the beam incident on the sample and of the radiation back scattered by the sample. FIGS. 2E and 2F illustrate a variation in the distance between the screen and the sample. FIG. 2G is an example of an optical system for shaping the laser beam.

Figure 3A:
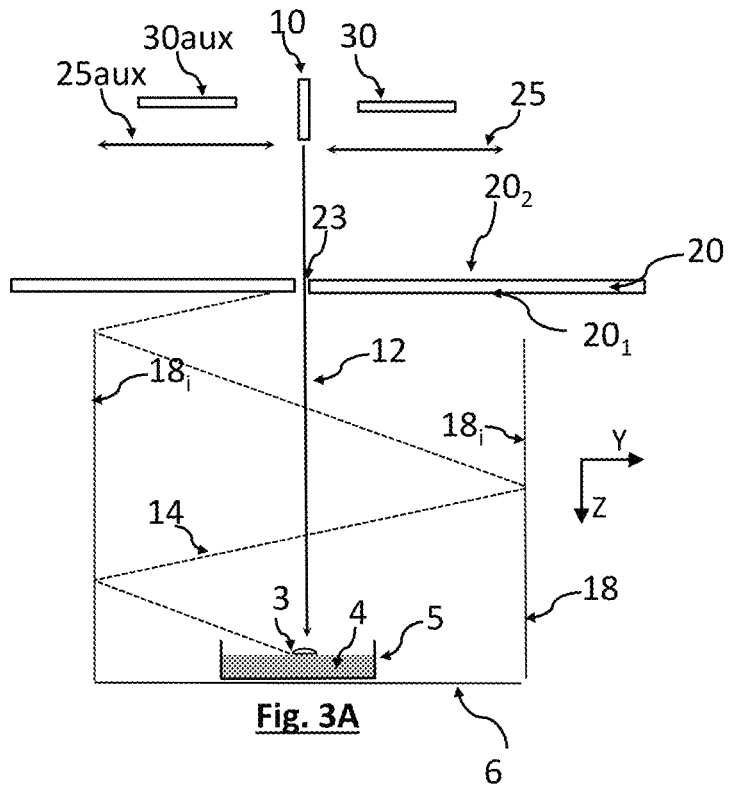
Figure 3B:
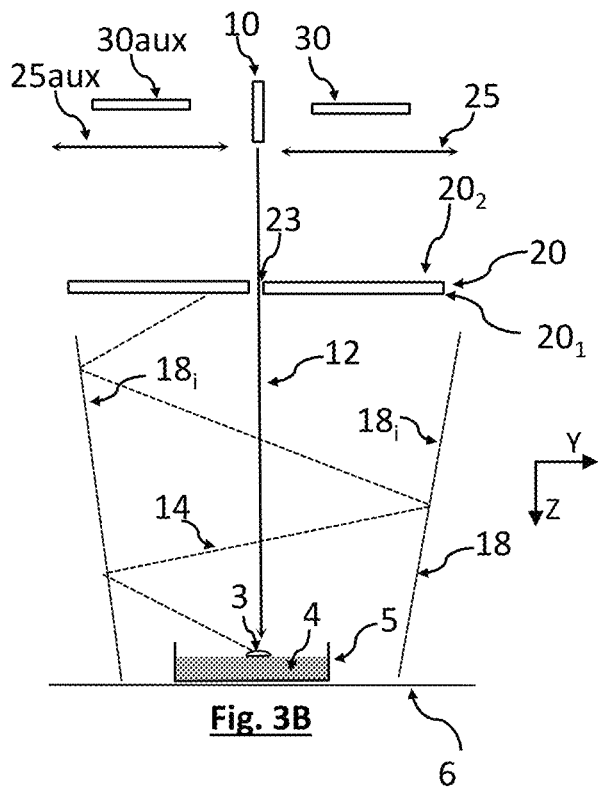
Figures 3C, 4A:
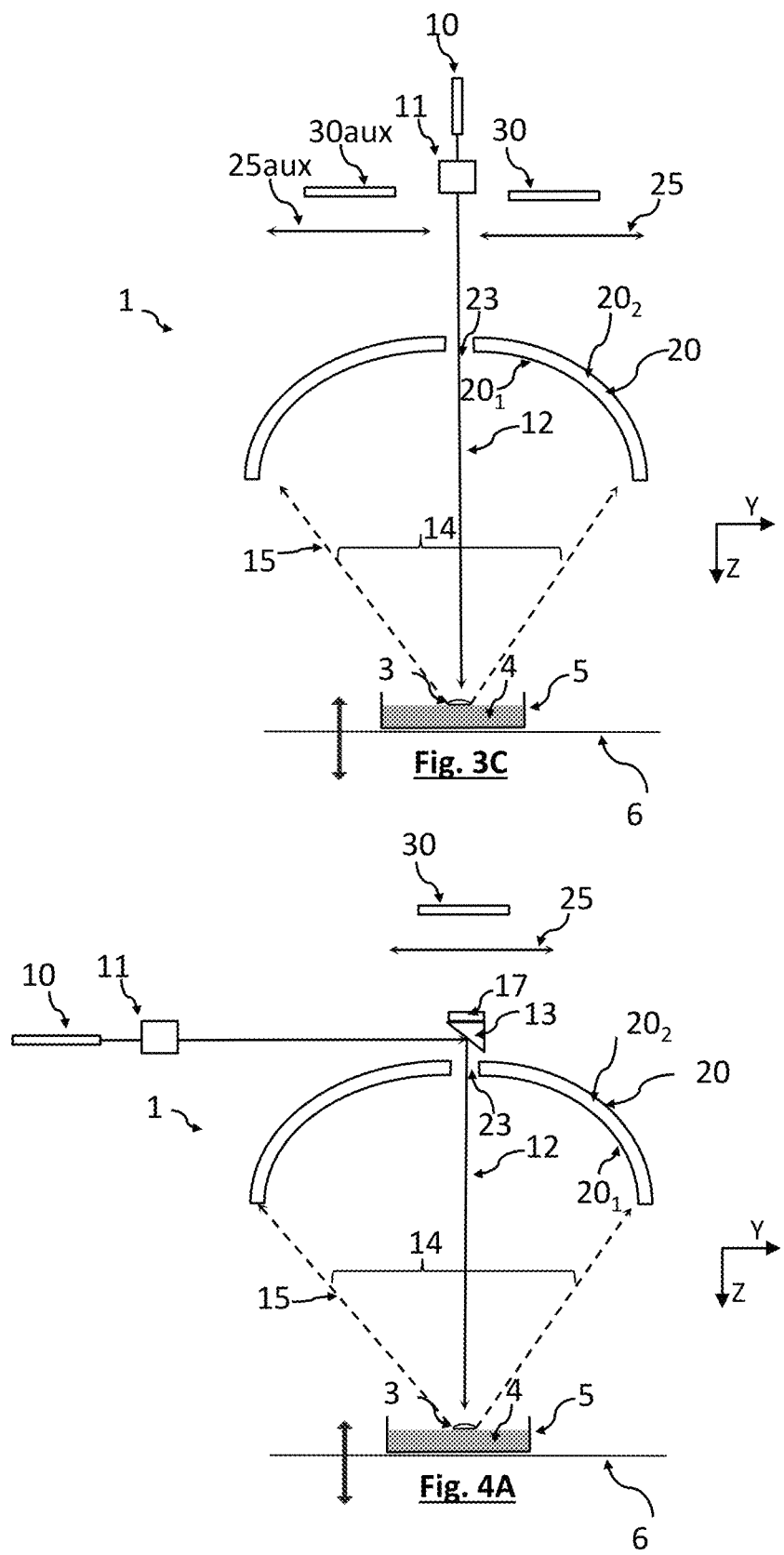

FIGS. 3A and 3B illustrate one variant of the embodiment. FIG. 3C shows another variant.

Figure 4B:
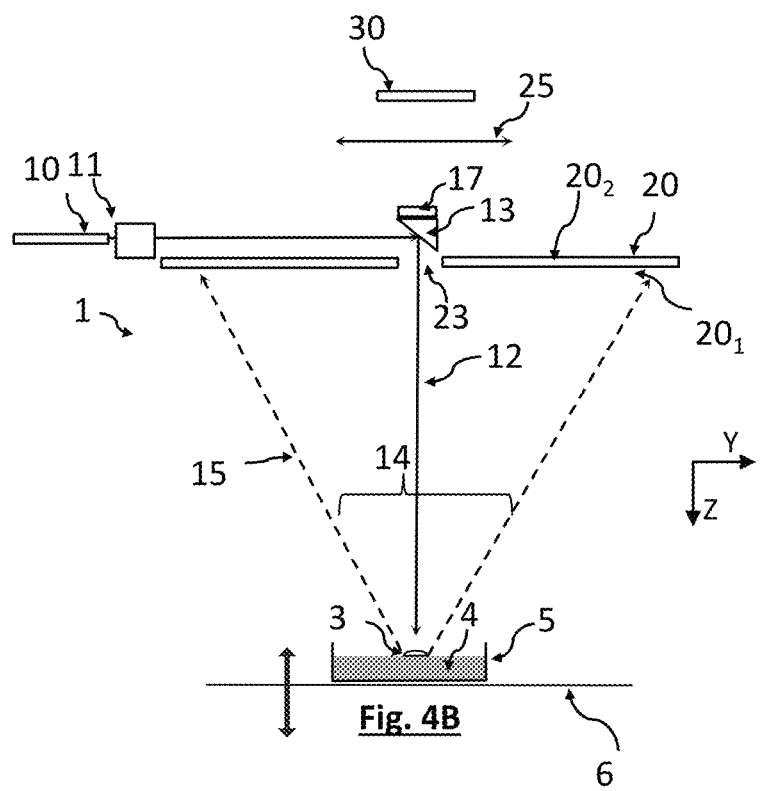

FIGS. 4A and 4B schematically show another embodiment.

FIGS. 5A, 5B, 5C and 5D show scattergrams obtained by implementing one embodiment of the invention.

Figure 6A:
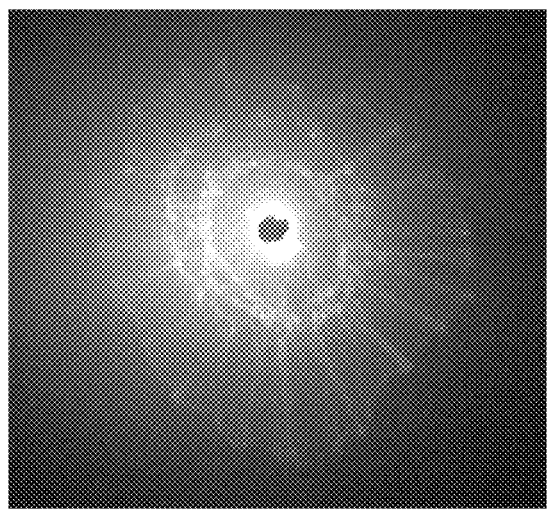
Figure 6B:
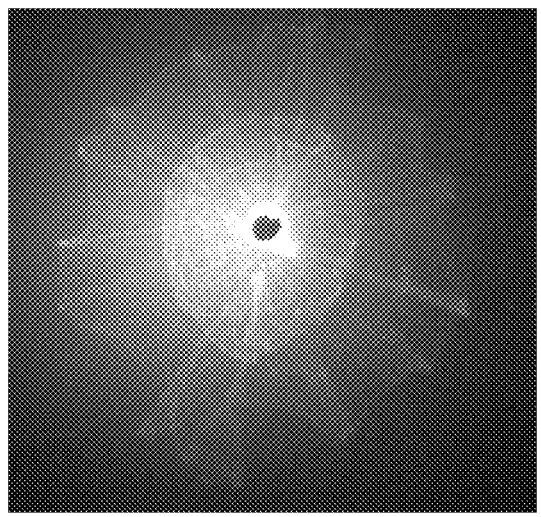

FIGS. 6A and 6B show scattergrams obtained by implementing another embodiment of the invention.

Figure 7A:
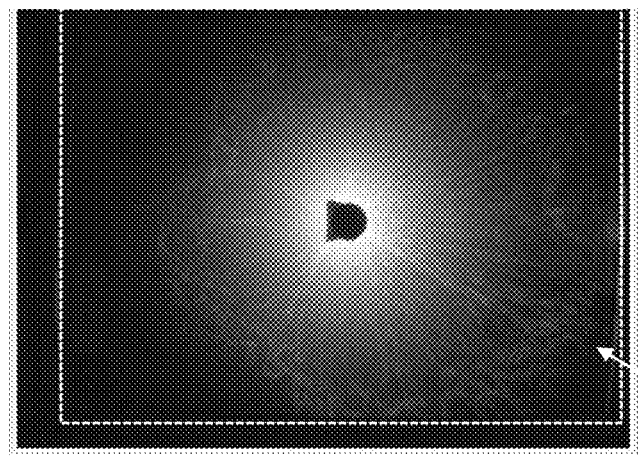
Figure 7B:
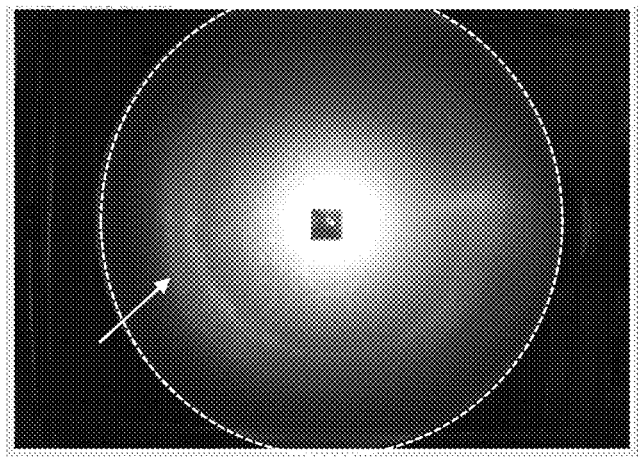

FIGS. 7A and 7B show scattergrams obtained by implementing two different configurations, respectively.

Figures 8A, 8B:
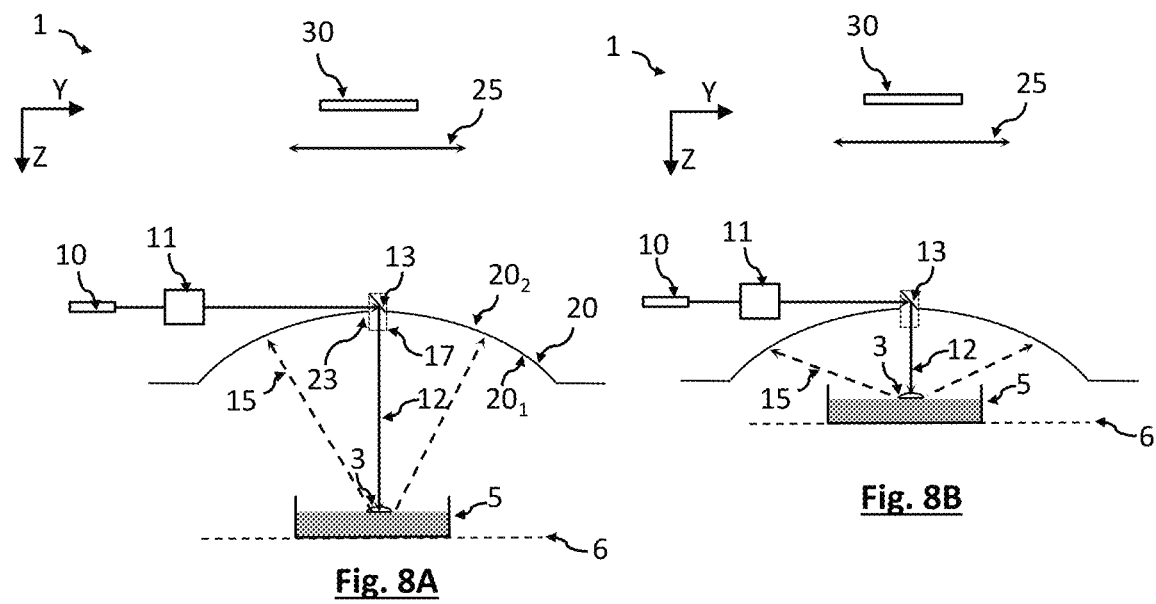

FIGS. 8A and 8B show a configuration implemented during experimental trials.

Figure 8C:
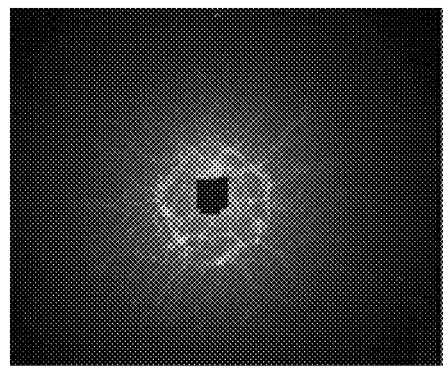
Figure 8D:
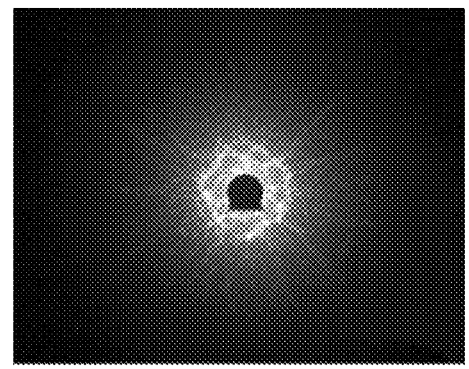

FIGS. 8C and 8D are scattergrams of a bacterial colony obtained using the configuration shown in FIG. 8A, with a curved screen, and a configuration such as shown in FIG. 4B, with a planar screen, respectively.

Figure 8E:
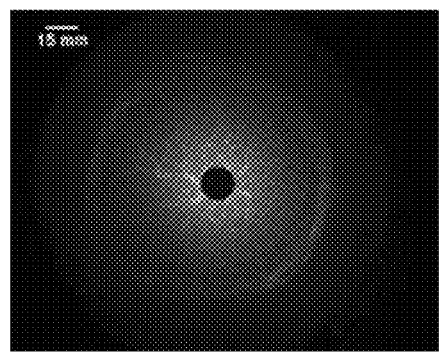
Figure 8F:
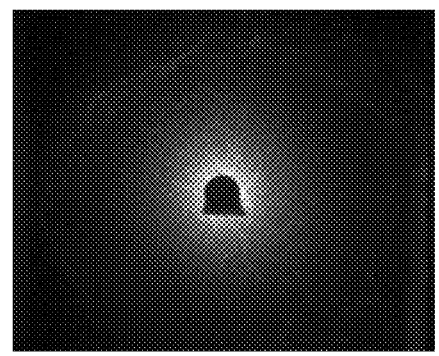

FIGS. 8E and 8F are scattergrams of a bacterial colony obtained using the configuration shown in FIG. 8B, with a curved screen, and a configuration such as shown in FIG. 4B, with a planar screen, respectively.

Figure 8G:
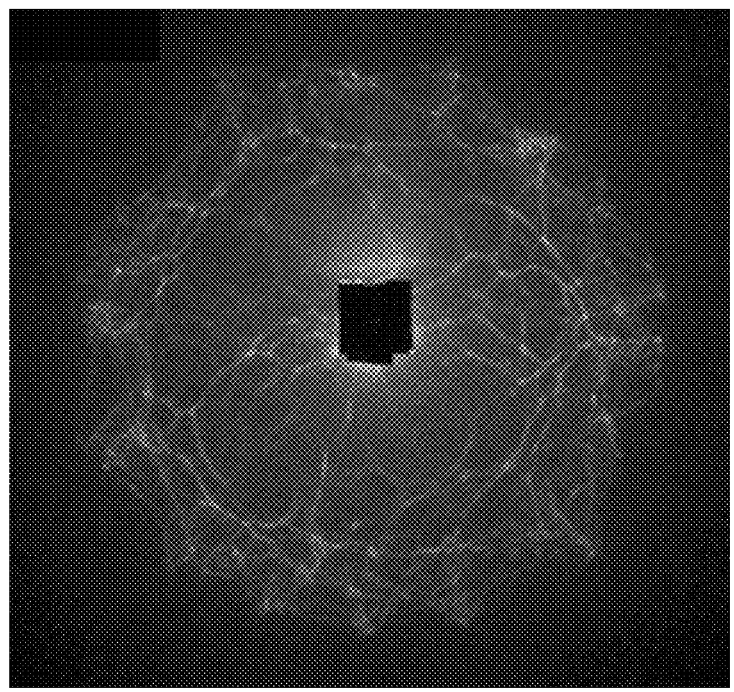

FIG. 8G is a scattergram of a bacterial colony obtained using the configuration shown in FIG. 8B.

DESCRIPTION OF PARTICULAR EMBODIMENTS

Figure 1A:
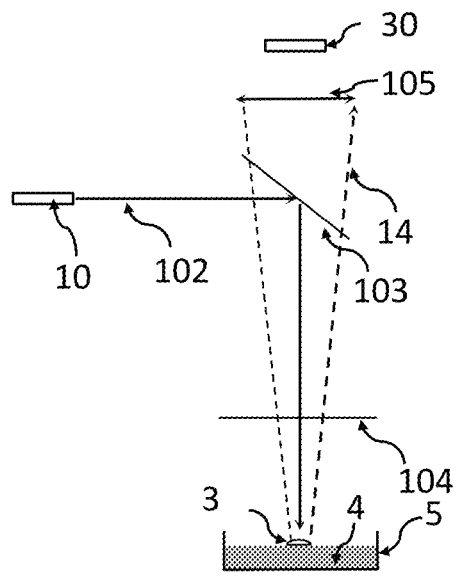
FIG. 1A shows a device for observing microorganisms according to the prior art.

FIG. 1A shows a device for observing microorganisms such as described in patent application WO2016/097063. A laser light source 10 emits a rectilinearly polarized light beam 102 that propagates to an object 3 to be characterized, for example a bacterial colony placed on the surface of a culture medium 4. Before reaching the bacterial colony 3, the polarized light beam 102 is deviated by a half-silvered mirror 103, so as to propagate in a direction, called the direction of incidence, substantially perpendicular to the surface of the culture medium 4. The light beam 102 passes through a quarter-wave plate 104 before reaching the bacterial colony 3. The light beam 102 interacts with the bacterial colony 3, this resulting in the formation of back-scattered radiation 14 that propagates in a direction substantially opposite to the direction of incidence. The back-scattered radiation 14 is formed by multiple interactions of the light beam 102 with the colony 3, combining the effects of diffraction and elastic scattering in the colony. The back-scattered radiation 14 passes through the quarter-wave plate 104, then the half-silvered mirror 103, before being focused by an optical system 105 toward an image sensor 30. The image formed on the image sensor, which is called a scattergram, is representative of the back-scattered radiation 14. The scattergram may be considered a signature of the bacterial colony, allowing the bacteria forming the colony to be identified. This device, which is representative of the prior art, has been implemented by the inventors. The latter have shown that this device does not allow certain bacterial colonies to be satisfactorily observed.

Figure 1B:
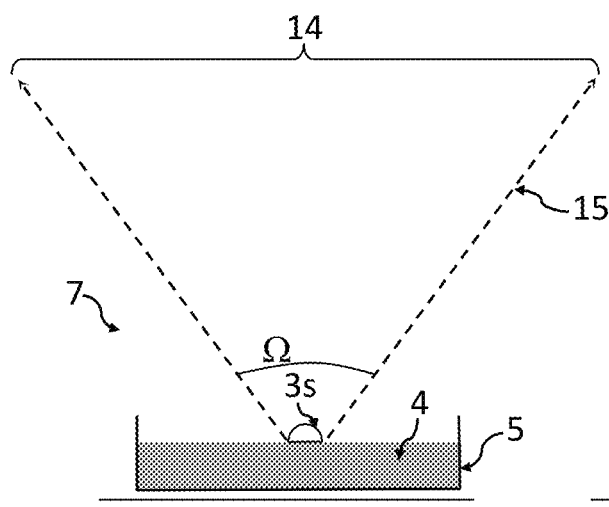
FIGS. 1B and 1C illustrate spatial distributions of back-scattered radiation emanating from two different objects, respectively.
Figure 1C:
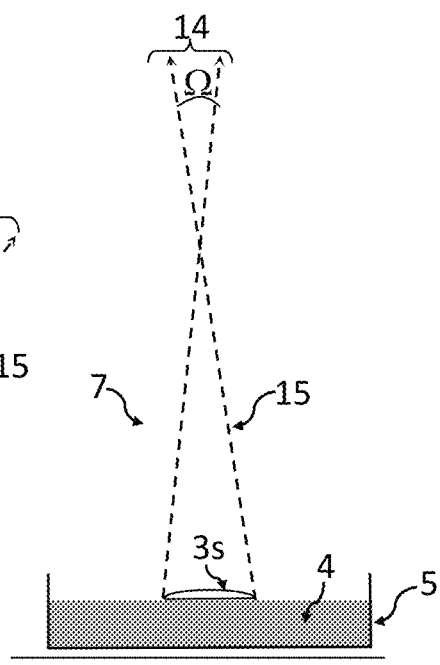

Specifically, the back-scattered radiation 14 is emitted in an angular range that varies depending on the type of microorganism observed. Certain bacterial colonies, for example a colony of Staphylococcus, develop by gradually forming an external surface 3s having a shape close to a hemisphere bounded by an ambient medium 7, for example air. Such a case is illustrated in FIG. 1B. In this type of configuration, the back-scattered radiation 14 is divergent, and forms a cone 15 covering a high angular range Ω. By high, what is meant is comprising angles larger than 65° or even than 85°. This is notably due to the refraction of the back-scattered radiation when it crosses the surface 3s in order to be refracted in the ambient medium 7. In contrast, as shown in FIG. 1C, other bacterial colonies develop by gradually forming a planar surface 3s, the radius of curvature of which is high. Thus, the back-scattered radiation 14 is refracted in the ambient medium 7 and propagates through the latter in a convergent beam, forming a cone 15, of apex angle Ω. Bacteria of Enterobacteriaceae type form colonies having such a morphology. Thus, depending on the type of observed microorganisms and their stage of development, the morphology of a colony varies, affecting the spatial distribution of the back-scattered radiation 14. One limit of the device described in WO2016/097063 is that the field of view is small and fixed, making it unsuitable for bacterial colonies the shape of which is similar to that of the example of FIG. 1B. The inventors have defined an observing device taking into account the variability of the spatial distribution of the back-scattered radiation 14. More precisely, the device, according to the invention, has a field of view that may be adapted to the observed microorganism. Specifically, the inventors have established that for microorganisms that generate back-scattered radiation the spatial distribution of which is illustrated in FIG. 1B, a very large field of view may be necessary.

FIG. 2A shows a first embodiment of a device 1 according to the invention. The device comprises a light source 10, able to emit a light beam 12, called the incident beam, that propagates to a sample 2 comprising an object 3 to be characterized. The light source 10 is preferably temporally and spatially coherent. The light source 10 is preferably a laser source. According to one variant, the light source may be a light-emitting diode or a white light source. It is then preferable for the light source to be sufficiently point-like to be spatially coherent. This may be obtained by associating the light source 10 with a spatial filter, for example a diaphragm, or an optical fiber. The light source 10 may also be associated with a bandpass filter, so as to obtain a sufficiently narrow emission spectral band $\Delta\lambda$, preferably one narrower than 50 nm or even than 10 nm. The light source is advantageously coupled to a system for forming the laser beam 11, as described below with reference to FIG. 2G.

The incident beam 12 emitted by the light source and that propagates toward the object 3 is preferably a parallel beam, the diameter of which may advantageously be adjusted. The diameter of the incident beam 12 is preferably comprised between 100 µm and 10 mm. The adjustment of the diameter allows allowance to be made for the size of the object 3 to be characterized. Thus, when the object 3 is a bacterial colony, this allows the size of the incident beam 12 to be adjusted to the morphology of the colony, the latter depending on the type of bacteria and on the stage of development. A forming optical system 11 may be placed between the light source 10 and the object 3. An example of a forming optical system is given with reference to FIG. 2G. The forming optical system 11 may allow the diameter of the incident beam 12 to be adjusted with respect to the object 3, in particular its size or its morphology. It may also allow the uniformity of a spatial distribution of the energy in the incident beam 12 to be increased, so that the light intensity in the beam is more uniform. The incident beam 12 propagates toward the object through an aperture 23 in a screen 20, the function of which is described below. The diameter of the aperture 23 is preferably smaller than 2 cm, and is for example smaller than 1 cm. Preferably, the diameter of the aperture 23 is adjusted so as to be larger than the diameter of the incident beam 12, while being as close as possible thereto. The light source 10 is placed so as to emit an incident beam 12 that propagates toward the object 3 and that reaches the latter at an orthogonal or a substantially orthogonal incidence.

The object to be characterized 3 may be a microorganism or a set of microorganisms forming a colony. The microorganism may be a bacteria, a yeast, a fungus or a microalgae. The object to be characterized may also be a group of cells, forming for example a cluster. The object to be characterized may make contact with a culture medium 4, either being placed in the latter or on the surface of the latter. The culture medium 4 is confined in an enclosure 5. The culture medium 4 and/or the enclosure 5 may be opaque or translucent. In particular, it is not necessary for the culture medium 4 and the enclosure 5 to be transparent, which is a condition of the methods based on transmission configurations described with respect to the prior art. The assembly formed by the enclosure 5, the culture medium 4 and the object 3 forms the sample 2, the latter resting on a holder 6. In the example shown, the holder is a planar stage that is translationally movable along an axis Z, called the axis of incidence. The invention is particularly suitable for samples comprising an opaque culture medium 4. When the culture medium 4 is not sufficiently opaque, it is preferable for the enclosure 5 to be opaque, and preferably absorbent, so as to minimize parasitic reflections. The enclosure 5 may comprise a cover, provided that the latter is transparent. When the enclosure 5 is transparent, it is preferable for it to be placed on a translucent or opaque holder 6. Such a holder prevents parasitic reflections.

Under the effect of the illumination by the incident beam 12, the object 3 emits back-scattered radiation 14 that propagates along or about a central back-propagation axis −Z that is parallel to the axis of incidence Z, and in the opposite direction to the latter. Generally, the term back-scattered radiation designates radiation that propagates along an propagation axis comprising a component opposite to the axis of incidence Z. The back-scattered radiation 14 results from the interaction of the photons of the incident beam 12 with the object 3, the latter having a refractive index higher than the refractive index of the ambient medium 7 through which the incident beam propagates, the ambient medium 7 generally being air. Because of the angle of incidence, most of the incident beam 12 penetrates into the object 3, thereby forming a refracted incident beam. The incident beam 12 refracted in the object 3 undergoes one or more elastic scatters in the object, and may generate diffraction waves. Back-scattered radiation 14 emanates from the object and propagates through the surface $3s$, as described with reference to FIGS. 1B and 1C. The back-scattered radiation is reflected in the ambient medium 7, then propagates, about the back-propagation axis −Z, to a screen 20, on which it forms an image $I_{20}$, called a scattergram, that is representative of the back-scattered radiation. The back-propagation axis is coaxial to the axis of incidence. In the literature, the image referred to here as a scattergram is also termed a scattering pattern or scatterograph. It will be noted that no focusing or image-forming optic is placed between the object 3 and the screen 20.

The screen 20 is able to collect the radiation 14 back scattered by the object 3 when it is illuminated by the light beam 12. The term screen designates an element a first face $20_1$ of which collects the back-scattered radiation 14, the latter being projected onto said first face $20_1$. Thus, the scattergram $I_{20}$ forms on the first face $20_1$ of the screen 20.

The screen 20 has, in the XY plane of the sample, an area of at least 50 cm$^2$, but it is preferable for its area to be larger than 100 cm$^2$, or even larger than 200 cm$^2$, and for example of 400 cm$^2$, i.e. a square of 20 cm side length. The incident beam 12 is preferably centered with respect to the object 3, in the XY plane of the sample.

The device comprises at least one image sensor 30, in order to acquire an image $I_{30}$ of the scattergram $I_{20}$ formed on the screen. The image sensor 30 may in particular be a matrix-array sensor comprising pixels arranged in a matrix array, each pixel forming one elementary photodetector. The image sensor 30 is for example a CCD or CMOS sensor. The image sensor 30 is connected to a processor 40, for example a microprocessor, comprising a memory 42 in which image-processing instructions are stored, these instructions allowing the image acquired by the image sensor 30 to be analyzed with a view to characterizing the object 3. The processor 40 may also allow the holder 6 to be moved with respect to the screen 20, as explained below. A monitor 44 allows the acquired image to be viewed.

In order to allow the scattergram to be projected onto the screen 20, the screen 20 is not completely transparent: it interacts with the scattered radiation 14, via absorption and/or scatter. Preferably, the screen transmits up to 80%, or even 90% or even 95% of the back-scattered radiation, the portion not transmitted being absorbed or scattered. The inventors believe that a transmittance of about 75% is optimal. By transmittance, what is meant is a ratio between an intensity of a radiation transmitted by the screen and an intensity of a radiation incident on the screen. The transmittance of the screen is preferably lower than 95%, or even lower than 90% or 80%. Opacity is defined as being the inverse of transmittance. The screen 20 comprises a second face $20_2$ that preferably lies parallel to the first face $20_1$. The screen 20 is configured such that the image projected onto the first face $20_1$, in the present case the scattergram, also appears, via transmission and/or scatter, on the second face $20_2$. The screen 20 then functions as a backlit screen, or a rear-projection screen, since it is interposed between the source of the scattered radiation, in the present case the object 3, and the image sensor 30. This screen 20 may be translucent, the term translucent designating a material that is not transparent, but that lets light pass, and through which elements appear hazy. It is for example a tracing-paper substrate, a substrate comprising scattering elements, for example microspheres, or even a fabric or a sheet of roughened glass. When the screen comprises microspheres, they may be microspheres made of polycarbonate. Rear-projection screens, taking the form of fabrics, suitable for this application are for example sold by Multivision under the references "retro gris" and "retro crème". When the screen 20 is a sheet of tracing paper, it may comprise a rough surface the Bendtsen roughness of which is 100 to 300 ml/mm, the Bendtsen roughness being determined according to standard NF 8791-2. The scattergram formed on the first face $20_1$ appears on the second face $20_2$, as shown in FIG. 2B.

The device comprises a focusing optic 25, allowing the scattergram $I_{20}$ formed on the second face $20_2$ of the screen 20, to be focused such that the image $I_{30}$ acquired by the image sensor 30 corresponds to this scattergram. Preferably, the image sensor 30 lies parallel to the screen 20, and the focusing optic 25 comprises an optical axis that is coaxial with the back-propagation axis −Z (or with the axis of incidence Z). However, in this embodiment, the image sensor 30 is not centered with respect to the back-propagation axis. Thus, in the image acquired by the image sensor 30, the scattergram may be deformed. Such a deformation may be corrected by algorithms based on a calibration, taking into account the position of the image sensor 30, and its optional inclination, with respect to the screen 20.

In the examples shown in FIGS. 2A, 2B, 2E and 2F, an image sensor called the auxiliary image sensor 30aux has been provided, this sensor allowing an auxiliary image $I_{30aux}$ of the scattergram to be formed. Preferably, the auxiliary sensor 30aux is placed symmetrically to the image sensor 30 about the axis of incidence Z. The auxiliary image sensor is optically coupled to the second face $20_2$ of the screen by an auxiliary focusing optic 25aux. The combination of the image $I_{30}$ acquired by the sensor 30 and the auxiliary image $I_{30aux}$ acquired by the auxiliary image sensor 30aux allows an image called the resulting image to be obtained, without deformation of the scattergram. The resulting image allows a scattergram having rotational symmetry to be obtained.

According to one variant, the image sensor 30 is movable and may occupy a plurality of positions about the incident beam 12, one image being acquired for each position. The combination of the images thus formed allows a resulting image, in which the scattergram appears not or not very deformed, to be obtained.

According to one variant, the screen 20 comprises a structured optical component, for example defining a Fresnel lens. A Fresnel lens comprises concentric annular structures arranged to focus an image of large diameter over a short focal length. The company DNP sells screens intended for back-scatter applications, based on one or both of the faces of the screen having optical lenses structured therein. These screens are referred to as optical rear-projection screens. Such screens allow the quantity of signal collected by the image sensor to be increased.

According to one variant, the screen 20 comprises a plurality of light guides extending between the first face $20_1$ and the second face $20_2$, in order to convey the scattergram from the first face $20_1$ to the second face $20_2$. It may be a question of a fiber-optic panel comprising an array of optical fibers extending, one beside the other, between the first face $20_1$ and the second face $20_2$. The size, in the XY plane, of such a screen may reach several hundred cm², for example 32.5 cm×32.5 cm. The diameter of each optical fiber is comprised between 5 µm and 25 µm, the numerical aperture being comprised between 0.92 and 1. Such panels are for example sold by Schott.

FIG. 2C shows a screen formed from two layers: a lower layer 21, defining the first face $20_1$ of the screen, and an upper layer 22 defining the second face of the screen $20_2$. The lower layer 21 may be scattering, for example because it consists of a roughened sheet made of glass or plastic, the roughened surface corresponding to the first face $20_1$. The upper layer 22 may form a Fresnel lens or a transparent sheet made of glass, playing the role of protective layer. It is not necessary for the upper layer to have an aperture 23, because it is transparent.

FIG. 2D shows a detail of the aperture 23, and the incident radiation 12 and the back-scattered radiation 14. The incident radiation 12 propagates to the object 3, along an axis Z, called the axis of incidence. The axis of incidence Z is substantially perpendicular to the surface 3s of the object 3 to be observed, or substantially perpendicular to an XY plane, called the plane of the sample, in which the culture medium 4 of the sample 2 lies. By substantially perpendicular, what is meant is perpendicular to within an angular tolerance, the latter preferably being lower than ±30°, or preferably lower than ±20°. Thus, the incident light beam 12 reaches the object 3 at an angle of incidence substantially equal to 90°, to within the angular tolerance. The back-scattered radiation 14 emanating from the object 3, and which takes the form of a cone 15 of apex angle Ω has also been shown. It comprises a first component, denoted $14_1$, and designated by the term "reflection component", corresponding essentially to specular reflection of the incident beam 12 from the surface of the sample, to which is added diffraction of order 0. It comprises a second component $14_2$, lying about the first component, the second component $14_2$ containing information that may be used to characterize the object 3.

The aperture 23 in the screen is dimensioned depending on the diameter of the incident beam 12 emitted by the light source 10. Some of the back-scattered radiation 14 does not propagate to the screen 20, and therefore does not appear in the scattergram, because of the presence of the aperture 23. This blocks transmission of the first component $14_1$ of the radiation back scattered toward the screen. However, as indicated above, the first component $14_1$ essentially represents specular reflection of the incident beam 12 from the object 3; it contains no, or little, information that is useful with respect to characterizing the observed object 3. In addition, this first component is generally bright. Its non-transmission toward the screen 20 allows a bright and uninformative contribution to the scattergram to be blocked. This improves the dynamic range of the scattergram. The masking, by the aperture 23, of the reflection component $14_1$ appears, in the scattergrams, in the form of a shadow. This shadow is indicated by a black arrow on the scattergram shown in FIG. 2B.

The distance d between the sample 2 and the screen 20 is advantageously variable, as illustrated in FIGS. 2E and 2F. Specifically, as indicated above, the spatial distribution of the back-scattered radiation 14 may vary, the latter possibly taking the form of a cone 15 of relative openness extending divergently or convergently from the object. Thus, the holder 6 of the sample may be mounted on a translatable stage that permits a translation parallel to the axis of incidence Z. FIGS. 2E and 2F show a sample 2 located at a first distance $d=d_1$ and at a second distance $d=d_2$ from the screen 20, with $d_1>d_2$. The movement of the holder 6 may be controlled by the processor 40. The range of variation in the distance is typically 3 cm to 20 cm, or even 30 cm. The distance is determined depending on the scattergram formed on the screen 20, so that the scattergram extends over the largest possible area, while remaining compatible with the field of view of the image sensor 30, the latter depending on the size of the image sensor and of the focusing optical system 25.

The distance may be adjusted manually, or by implementing an algorithm based on recognition of the outline bounding the scattergram. Such an algorithm may for example use a Canny filter. When this outline has been detected, the distance is adjusted so as to make the area of the scattergram, on the screen 20, exceed a preset threshold value. The adjustment of the distance d makes it possible to take into account the variability in the back-scattered radiation due to the various types of objects to be characterized. According to one embodiment, once an optimal distance has been determined, allowing the area of the scattergram projected onto the screen to be maximized, an image of the scattergram is acquired. The distance is then increased, so as to verify the absence of back-scattered radiation outside of the scattergram observed beforehand, i.e. that corresponding to the optimal distance.

Preferably, the holder 6 is also movable in the XY plane of the sample. This allows the incident light beam 12 to be centered on the object 3. This allows an analysis to be carried out whatever the position of the object 3 in the sample 2. Such centering may be adjusted depending on a symmetry criterion of the scattergram. Specifically, when the incident beam is centered on the object, the scattergram present on the screen has a symmetry of revolution. The symmetry may for example be quantified via the shape of the outline of the scattergram.

Whatever the embodiment, a forming optical system 11 may be associated with the light source 10, so as to form a collimated incident beam 12, according to principles known to those skilled in the art. FIG. 2G shows an example of a forming optical system. It comprises a succession of conventional optical components: an achromatic lens 110, a pinhole 111 of 50 μm diameter, a convergent lens 112 and a beam expander 113. The forming optical system 11 may comprise, optionally, a flat-top beam converter 114 followed by a beam reducer 115. The beam expander 113 allows the size of the laser beam to be adjusted, so that the latter approaches the size of the object to be observed. The expander 113 may consist of a set of two lenses of variable focal length, which is programmable by the processor 40. The beam converter 114 allows the distribution of the intensity in the beam to be adjusted.

The spatial distribution of the back-scattered radiation 14 may vary significantly depending on the observed object. In certain cases, it extends over a very high angular range on either side of the axis of incidence Z. This is in particular case when the object, in the present case a bacterial colony, has a curved morphology, such a morphology for example being observed in bacterial colonies of *Staphylococcus*. In such a case, the size of the screen 20 must be large in order to obtain a complete scattergram, in particular taking into account large back-scatter angles (typically larger than 65°). The expression "back-scatter angle" is understood to mean the angle between back-scattered radiation 14 emanating from the object and the axis of incidence Z. It is also possible to adjust the distance between the screen 20 and the object 3, as indicated above. This notably allows a scattergram the diameter of which corresponds to a preset template, for example a diameter comprised between 15 and 20 cm, to be obtained. FIG. 3A describes a variant allowing a reasonable size to be preserved for the screen 20 while allowing back-scattered radiation 14 emanating from the object at large back-scatter angles to be taken into account. According to this variant, an annular reflector 18, extending parallel to the axis of incidence Z, is placed between the object 3 and the screen 20, around all or some of the object 3. The annular reflector 18 allows some of the radiation 14 back scattered toward the screen 20 to be reflected. It may be a question of a tubular reflector that is coaxial with the axis of incidence Z. FIG. 3A shows a cylindrical annular reflector. Its height and its diameter may be 6 cm and 17.5 cm, respectively. It may be a question of a cylinder the internal wall 18*i* of which is reflective. For example, a thin metal layer, for example of aluminum, may have been deposited on the internal wall 18*i*. The annular reflector 18 may also be of conical shape, as shown in FIG. 3B. Such a conical reflector may have a small diameter equal to 19 cm, a large diameter equal to 20 cm, and a height of 3 cm. The angle of inclination of the internal wall, with respect to the axis Z, is for example 13°. The angle of the internal wall 18*i* may be dimensioned such that the back-scattered radiation 14 having the largest back-scatter angle undergoes only a single reflection before reaching the screen 20. Preferably, at least one diameter of the annular reflector 18 is larger than two times the diameter of the enclosure 5.

FIG. 3C shows a variant able to be used in addition or as an alternative to the annular reflector described with reference to FIG. 3A or 3B. According to this variant, the screen 20 is not planar and has a curved shape that curves toward the sample 2. This also facilitates a collection, by the screen, of radiation back scattered at large back-scatter angles. The curvature of the screen 20 may be regular or not. The screen may for example have a dome shape. The screen may also describe a curvature having planar facets.

By curving toward the sample, what is meant is that the screen describes a curvature the center of which is located between the sample and the screen, or more generally in a half-space bounded by the screen and comprising the sample. Thus, the screen has a concave shape, so as to define a space lying between the screen and the sample, this space being such that, whatever two points of said space are considered, the segment connecting said points is included in the space.

FIG. 4A shows one embodiment in which the screen 20 is curved, as described with reference to FIG. 3C. The device comprises a reflective element 13, which receives the incident beam emitted by the light source 10 and reflects it toward the object 3, at an angle of incidence Z. In this example, the incident beam 12 is emitted in a direction parallel to the surface of the culture medium 4, then is reflected toward the sample at an incidence normal to the latter. One advantage of this embodiment is that the image sensor 30 and the optical system 25 may be centered with respect to the axis of incident Z, this amounting to centering them with respect to the axis of back scatter –Z. This allows a symmetric image of the scattergram formed on the screen 20 to be acquired, with a single image sensor. It is then possible for the acquired image to preserve an invariance in rotation. When the screen 20 is curved, the optical system 25 is preferably a large-angle objective, allowing a high depth of field to be obtained so as to form a clear image of the scattergram appearing on the second surface of the screen 20$_2$. The aperture 23 is preferably located at the apex of the screen 20.

The area of the reflective element 13 is the smallest possible, so as to not interfere with the back-scattered radiation 14 emanating from the object 3. It is preferably smaller than 5 cm$^2$, and even more preferably smaller than 2 cm$^2$, or even smaller than 1 cm$^2$. The area of the reflective element 13 is preferably suitable for the diameter of the beam emitted by the light source 10. The reflective element 13 may be fastened to a holder 17. Preferably, the reflective element 13 and/or the holder 17 to which it is fastened absorb at least 30%, and advantageously at least 50%, or even 80% or 90% of the back-scattered radiation 14 emitted by the object. This allows a transmission of the first component 14$_1$ of the back-scattered radiation, which component was described above, of the back-scattered radiation 14, to the image sensor 30 to be avoided.

FIG. 4B shows a variant of this embodiment, in which the screen 20 is flat.

The image obtained on the image sensor 20 may allow the object 3 to be characterized. The characterization may be an identification. To this end, characteristics of the image are determined, and compared to calibration characteristics established on standard objects. These characteristics may also be the subject of a classification on the basis of said calibration characteristics. Patent application WO2014184390 describes a method for classifying bacterial colonies based on a projection of the image onto a basis of orthogonal Zernike polynomials. Other classifying algorithms, for example allowing a principal-component analysis to be obtained, are envisionable. The objective of such a classification is to decrease the spatial information in the image into a set of coordinates, on the basis of which the identification of the microorganism is obtained.

Experimental Trials

Experimental trials have been carried out, implementing the embodiment shown in FIG. 4A. The main components used were the following:

light source 10: laser source of reference LCGFP-D-532-10C-F—supplied by Laser components.

Forming optical system 11: achromatic lens Thorlabs AC254-030-A-ML—A280TM-A; pinhole Thorlabs—P50 S, convergent lens Thorlabs A280TM-A.

Sample enclosure: petri dish of 90 mm diameter—Biomérieux.

Focusing optical system: LM5JC10M—Kowa.

Camera: UI-1492ME—IDS or AVGT3300—Allied Vision.

Reflective element: mirror inclined at 45°.

The assembly is placed in the dark.

During these trials, various types of bacterial colonies were observed. During each operation, the incident laser beam 12 was centered on the colony visually, by the operator.

FIGS. 5 A to 5D are examples of images of scattergrams obtained by observing bacterial colonies developing on a Columbia blood agar (CBA) such as described with reference to the prior art. The screen 20 used was of dome shape, and was made of rough glass. It was a question of a translucent, nontransparent screen. The circular border of the screen has been shown, in each of these figures, by a dashed white outline. The bacterial colonies observed in each of these figures are the following.

Figure 5A:
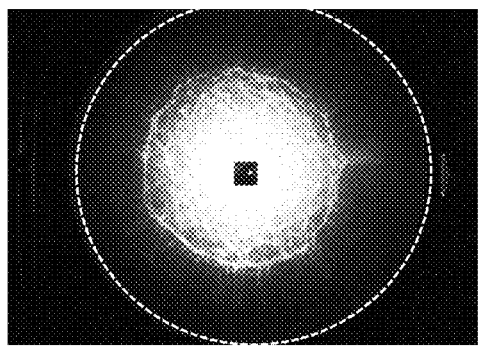
Figure 5B:
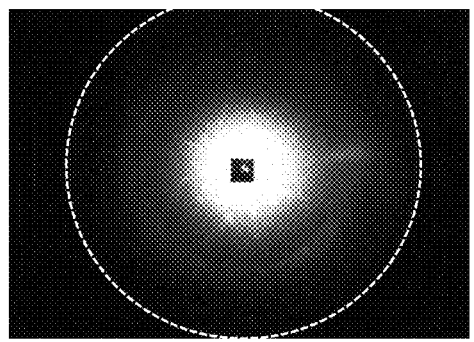
Figure 5C:
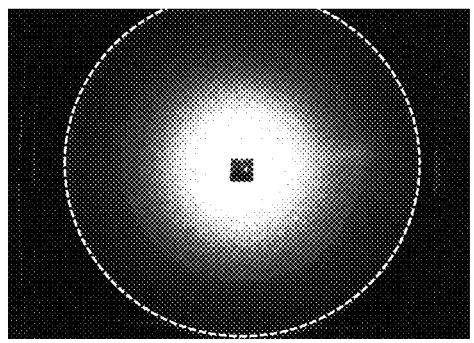
Figure 5D:
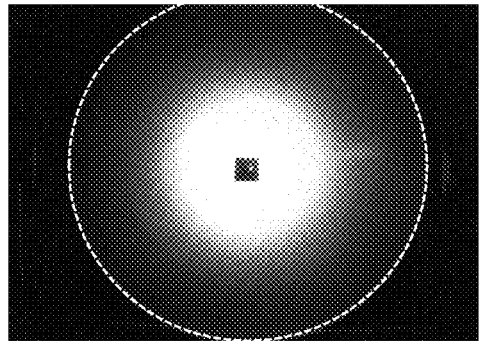

FIG. 5A: *Staphylococcus maltophilia;*
FIG. 5B: *Staphylococcus saprophyticus;*
FIG. 5C: *Staphylococcus warneri;*
FIG. 5C: *Pseudomonas putida.*

The scattergram of each colony was entirely projected onto the screen 20, without exceeding the latter, this allowing a complete image to be acquired using the image sensor 30. The distance between the apex of the screen and each colony was 4 cm. The diameter of the laser beam was 1 mm.

FIGS. 6A and 6B were obtained by implementing the embodiment described with reference to FIG. 2A, without the auxiliary image sensor 30 aux. The screen 20 used was a planar sheet of tracing paper. The main components of the device were those listed above. The observed bacterial colonies, which were developing on a CBA culture medium, were:

FIG. 6A: *Escherichia coli;*
FIG. 6B: *Pseudomonas putida.*

Images of scattergrams that were exploitable, but that had an asymmetry because of the offset of the image sensor 30 with respect to the axis of back scatter (−Z) were obtained. The exposure time of each image was 136 ms. The distances between the colony and the screen were 10 cm (FIG. 6A) and 7.5 cm (FIG. 6B), respectively.

The trial results shown in FIGS. 7A and 7B allow an embodiment implementing a planar screen 20, such as shown in FIG. 4B, to be compared with an embodiment integrating a dome-shaped screen 20, such as shown in FIG. 4A. In each trial, the device components listed in relationship to FIGS. 5A to 5D were used. In each of these figures, the shadow formed by the reflective element 13 and its holder 17 may be seen at the center of the scattergram. The bacterial colony was a colony of *Stenotrophomonas maltophilia* on a CBA culture medium. In the device employing a planar screen, such as shown in FIG. 4B, the screen 20 was a "retro gris" fabric as supplied by Multivision. The distance between the screen 20 and the colony was small, smaller than 1 cm, the colony almost making contact with the screen. The scattergram shown in FIG. 7A was obtained. The border of the screen 20 is indicated in the image by a dashed white frame. The white arrow indicates the periphery of the scattergram. Such a bacterial colony produces back-scattered radiation 14 that is emitted at large back-scatter angles with respect to the axis of the incident beam, these angles exceeding 65°. A scattergram that extends right up to the border of the screen results.

When the embodiment using a dome-shaped screen 20, such as shown in FIG. 4A, is used the scattergram is more compact, as shown in FIG. 7B. In this trial, the screen 20 described above with reference to FIGS. 5A to 5D was used. The shape of the screen allows a complete scattergram, including high back-scatter angles, to be formed.

During another series of trials, scattergrams respectively obtained using a screen 20 describing a segment of a dome and a flat screen were compared. FIGS. 8A and 8B illustrate a configuration similar to that described with reference to FIG. 4A. The screen 20 used was an acrylic screen provided by Draper Inc, namely a ¼"acrylic IRUS screen—custom vacuum formed—Cine25 tint—HC coating. An aperture 23 of 15 mm diameter was produced at the apex of the screen. Into the aperture, a cylindrical holder 17, holding a reflective element 13, was inserted. The latter allowed the incident beam 12 to be reflected toward the analyzed object 3. As indicated above, the object was movable with respect to the screen. It was placed on a holder 6 that was able to be translated with respect to the screen 20, depending on the cone 15 formed by the radiation back scattered by the object. When the angle at the apex of the cone 15 was small, the object could be moved far from the screen (FIG. 8A) so that the area of the scattergram appearing in the image of the image sensor 30 was sufficiently extensive. In contrast when the angle at the apex of the cone 15 was large (FIG. 8B), the object could be moved close to the screen, so that the back-scattered radiation, emitted at a high back-scatter angle, could be represented in the scattergram. The diameter of the incident beam 12 was 2 mm, the luminous power being 4 mW.

FIGS. 8C and 8D show the scattergrams obtained using the image sensor 30 respectively in a configuration such as shown:

in FIG. 8A;

and in FIG. 4B, employing a flat screen made of the same material, and having the same tint, and the same surface coating as the curved screen described with reference to FIGS. 8A and 8B.

The sample was a bacterial colony of *Pseudomonas putida*, which produced back-scattered radiation in a cone 15 a relatively small angle. The culture medium was CBA, which was described above. The exposure time was 600 ms (FIG. 8C) and 900 ms (FIG. 8D). The images are of good quality. It may be seen that the attenuation of the reflection component $14_1$ allows the scattergram, and in particular its periphery, to be suitably viewed without glare. This attenuation results in a shadow forming at the center of the images. Thus, saturation of the pixels of the image sensor with bright radiation is avoided, thus allowing less intense radiation, for example as present on the periphery of the scattergram, to be seen.

FIGS. 8E and 8F shows scattergrams respectively obtained using the image sensor 30 in a configuration such as shown:

in FIG. 8B;

and in FIG. 4B, employing a flat screen made of the same material, and having the same tint, and the same surface coating as the curved screen described with reference to FIGS. 8A and 8B.

The sample was a bacteria colony of *Stenotrophomanas maltophilia*, which produced back-scattered radiation of relatively large angle. The culture medium was CBA, which was described above. It may be seen that the attenuation of the reflection component $14_1$ allows the scattergram, and in particular its periphery, to be suitably viewed without glare. In addition, comparing these two figures, the curved shape of the screen 20 (see FIG. 8E) allows more of the back-scattered radiation emitted at large angles with respect to the angle of incidence of the beam 12 to be collected. The scattergram obtained is more complete.

FIG. 8G shows a scattergram of two *Yersinia ruckeri* colonies, which was acquired with a device according to FIG. 8B. This figure allows the quality of the image obtained using the curved screen to be assessed.

Since the method is nondestructive, a plurality of images of a given bacterial colony, at various stages of incubation, may be produced, so as to assess the propensity of the colony to develop, or its ability to resist an antibiotic or antibacterial agent. In this case, the characterization of the object represents the tendency of the latter to develop.

The method may also allow the number of objects present on the surface of a sample to be counted.

The invention will possibly be implemented to assist with various types of examinations, such as sterility tests, antibiotic susceptibility tests, antibacterial or bacteriophage susceptibility tests, to target antibacterial substances, for identification purposes, or for counting purposes. The invention may also be applied to the observation and characterization of other types of microorganisms, such as yeast, fungi, or microalgaes.

The invention claimed is:

1. A device for observing an object, present in a sample, comprising:
    a support, configured to receive the sample;
    a light source, configured to emit an incident light beam, in order to illuminate the object;
    an image sensor, configured to acquire an image representative of radiation back scattered by the object under the illumination by the incident light beam;
    wherein the device further comprises:
        a screen, facing the support, so as to be exposed to radiation back scattered by the object when the object is illuminated by the incident light beam, so as to form, on the screen, a scattergram, representative of said back-scattered radiation;
        the screen comprising a first face exposed to the back-scattered radiation;
        the screen disposed between the light source and the object, and comprising an aperture, through which the incident light beam propagates before reaching the object, the screen comprising a second face, so that the scattergram formed on the first face appears on the second face;
        the image sensor being configured to acquire an image of the scattergram formed on the screen, the screen being placed between the image sensor and the object, the image sensor being coupled to the second face of the screen by a focusing optic; wherein
    the device further comprises a reflective element, configured to direct the incident light beam emitted by the light source toward the object, through the aperture, the reflective element being placed between the object and the image sensor,
    the image sensor, the reflective element, the aperture, and the object are aligned according to a single axis of incidence, along which the incident light beam propagates toward the object,
    (i) the reflective element absorbs at least 30% of the back-scattered radiation emitted by the object, along the axis of incidence, or (ii) the reflective element is fastened to a holder, the holder absorbing at least 30% of the back-scattered radiation emitted by the object, along the axis of incidence, and
    the image of the scattergram comprises a shadow, formed by the reflective element and/or the holder, the shadow blocking a specular reflection of the incident light beam.

2. The device as claimed in claim 1, wherein the incident light beam reaches the object at an incidence perpendicular or substantially perpendicular to the object, with an angular tolerance of ±30°.

3. The device as claimed in claim 1, wherein the image sensor is centered with respect to the axis of incidence.

4. The device as claimed in claim 1, wherein a diameter of the aperture is smaller than 2 cm.

5. The device as claimed in claim 1, wherein the screen has a curved shape.

6. The device as claimed in claim 1, wherein the screen is translucent.

7. The device as claimed in claim 1, wherein the screen comprises a light guide for conveying light between the first face and the second face.

8. The device as claimed in claim 7, wherein the screen comprises a plurality of optical fibers extending between the first face and the second face.

9. The device as claimed in claim 1, wherein the screen transmits less than 90% of the back-scattered radiation from the first face toward the second face.

10. The device as claimed in claim 1, wherein the support is movable with respect to the screen, a distance between the support and the screen being adjustable.

11. The device as claimed in claim 1, wherein the incident light beam propagates between the screen and the object about the axis of incidence, the device comprising an annular reflector, disposed around the axis of incidence, and disposed between the sample and the screen, the annular reflector being configured to reflect some of the back-scattered radiation toward the screen.

12. A method for observing an object present in a sample, the sample facing a screen comprising a first face, the method comprising:
    illuminating the object using an incident light beam emitted by a light source, the screen being disposed between the light source and the object, the incident light beam propagating to the object through an aperture in the screen;
    exposing a first face of the screen to radiation back scattered by the sample, so as to form, on the first face, a scattergram, representative of said back-scattered radiation, the screen comprising a second face, so that the scattergram formed on the first face appears on the second face;
    acquiring an image of the scattergram formed on the screen with an image sensor, the screen being disposed between the image sensor and the object, the image sensor being coupled to the second face by a focusing optic; wherein the incident light beam emitted by the light source is directed toward the object, through the aperture, by a reflective element;

the reflective element is placed between the object and the image sensor;

the image sensor, the reflective element, the aperture, and the object are aligned according to a single axis of incidence, along which the incident light beam propagates toward the object;

(i) the reflective element absorbs at least 30% of the back-scattered radiation emitted by the object, along the axis of incidence, or (ii) the reflective element is fastened to a holder, the holder absorbing at least 30% of the back-scattered radiation emitted by the object, along the axis of incidence; and the image of the scattergram comprises a shadow, formed by the reflective element and/or the holder, the shadow blocking a specular reflection of the incident light beam.

13. The method as claimed in claim 12, wherein the incident light beam reaches the object at an incidence perpendicular or substantially perpendicular to the object, with an angular tolerance of ±30°.

14. The method as claimed claim 12, wherein the image sensor is centered with respect to the axis of incidence.

15. The method as claimed in claim 12, wherein an area of the aperture is smaller than 2 cm$^2$.

16. The method as claimed in claim 12, wherein the screen is curved.

17. The method as claimed in claim 12, wherein:

the screen is translucent; or the screen comprises at least one optical fiber, extending between the first face and the second face; or one of said first face and said second face of the screen is structured so as to form a lens.

18. The method as claimed in claim 12, wherein the screen transmits less than 90% of the back-scattered radiation between the first face and the second face.

19. The method as claimed in claim 12, comprising, following the acquiring, a step of adjusting a distance between the sample and the screen depending on the image acquired by the image sensor, the illuminating, the exposing, and the acquiring being repeated after the adjustment of said distance.

20. The method as claimed in claim 12, comprising a step of characterizing the object based on the image acquired by the image sensor.

21. The method as claimed in claim 20, wherein the characterizing comprises:

determining characteristics of the image;

identifying the object using said characteristics and calibration characteristics established by implementing the illuminating, the exposing, and the acquiring of the method on a standard sample.

22. The method as claimed in claim 12, wherein the object comprises a microorganism.

23. The method as claimed in claim 12, wherein an area of the aperture is smaller than 1 cm$^2$.

* * * * *